US006261608B1

(12) United States Patent
Lee et al.

(10) Patent No.: US 6,261,608 B1
(45) Date of Patent: Jul. 17, 2001

(54) METHOD FOR MANUFACTURING REFINED FISH OIL

(76) Inventors: Sang Hak Lee, Woo-bang Apt. 106-205, Induk-dong 7, Nam-gu, Pohang City 790-350; Joo Yeon Lee, Hyundae Semicon, Apt. Ga-705, Bongmyeong-2dong, Hungduk-gu, Chungjoo City 361-302, both of (KR)

( * ) Notice: Subject to any disclaimer, the term of this patent is extended or adjusted under 35 U.S.C. 154(b) by 0 days.

(21) Appl. No.: 09/472,154

(22) Filed: Dec. 27, 1999

(51) Int. Cl.[7] .............................. A23D 7/00; A61K 35/60

(52) U.S. Cl. ............................ 426/33; 426/488; 426/608; 424/523

(58) Field of Search ..................................... 424/489, 502, 424/523; 426/601, 608, 609, 643, 648, 488, 7, 54, 33

(56) References Cited

U.S. PATENT DOCUMENTS 5,693,358 * 12/1997 Park et al. ........................... 426/643

* cited by examiner

*Primary Examiner*—Keith Hendricks
(74) *Attorney, Agent, or Firm*—Stevens, Davis, Miller & Mosher, LLP

(57) ABSTRACT

Disclosed is a method for manufacturing refined fish oil by introducing a novel process into a phospholipid-deprived fish oil which is obtained by mixing fish oil with water and a monosodium glutamate (MSG) by-product with stirring, fermenting the mixture in the presence of urea, processing the mixture with steam, and centrifuging the mixture to separate water and phospholipids from the fish oil. The method further includes the steps of measuring acid value of the separated fish oil to neutralize the fish oil with NaOH, washing the deaciding fish oil with warm water, and drying the washed fish oil in vacuum; mixing the dehydrated fish oil with powders of earthworm excrement to absorb the fish oil into the powders, subjecting the mixture to reaction at least 30° C. or higher for 0.5–1 hour, bleaching the fish oil absorbed into the earthworm excrement powders by use of activated clay, and filtering the bleached fish oil through a filter; and deodorizing the bleached and filtered fish oil under a steam atmosphere in a high vacuum, deodorizing apparatus, cooling and filtering the fish oil and packaging it into closed vessel. The refined fish oil is slightly improved in acid value and peroxide value and thus can be preserved freshly for a relatively long period of time without offensive fish odor.

9 Claims, 1 Drawing Sheet

(I) Conventional refined fish oil (II) fish oil treated with MSG by-product and Urea (III) Present fish oil

METHOD FOR MANUFACTURING REFINED FISH OIL

FIELD OF THE INVENTION

The present invention relates to a method for manufacturing refined fish oil for use as a health subsidiary food.

BACKGROUND OF THE INVENTION

Extensive and steady research has found novel values from omega 3 fatty acids, including EPA (eicosa pentaenoic acid) and DHA (docosa hexaenoic acid), both found uniquely in fish oil, and they are now recognized as being highly valuable to the health of the body. A workshop on omega 3 and omega 6 fatty acids was held in Italy, 1988, under the supervision of Nutritional Science Section, International Biotechnology Institute of North Atlantic Treaty Organization (NATO), in which 120 scientists from 15 countries reached a consensus that omega 3 fatty acid should be supplied appropriately to the body and has a function of lowering cholesterol levels in blood in addition to being useful for anti-blood coagulation and anti-inflammation and rheumatoid arthritis treatment.

As mentioned, omega 3 fatty acid, which is contained in fish oil, is regarded as an essential fatty acid necessary to keep humans healthy. To be processed to a food or foodstuff, however, fish oil should typically be refined and deodorized on account of its characteristic offensive odor and ready liability to deterioration. In this regard, high techniques using expensive special apparatuses or high cost fermenting methods are used, so that an increase occurs in the production cost of refined fish oil, standing in the way of providing omega 3 fatty acid to many people at low costs.

The applicant has suggested an economically favorable method in removing fish odor and the utilization method of the deodorized fish oil as animal feed in Korean Patient Publication No. 93-779 entitled "A deodorization processing method of fish oil using mono sodium glutamate (MSG) by-product," which was matured into Korean Pat. No. 062232 on May 25, 1993, and Korean Patent No. 123840 entitled "Animal feed manufacturing method based on fish oil," yielded on Sep. 19, 1997, respectively.

In Korean Pat. Publication No. 93-779, it is described that an MSG by-product is mixed to fish oil together with water in order to remove phospholipid which is a main cause of fish smell contained in the fish oil. Then, the mixed resultant is heated to transpose oil-soluble phospholipids of the fish oil into water-soluble ones by means of water soluble protein in the MSG. The transposed water-soluble phospholipid is separated from the fish oil by a separation method, thereby floating its fat to an upper portion of the pure fish oil. If the floated fat is removed, the phospholipid contained in the fish oil is effectively eradicated.

The fish oil from which the phospholipid is removed is pre-heated at the atmosphere of vacuum. The odor of the fish oil is removed by water evaporation at the atmosphere of vacuum, to eliminate unsaturated fatty acid. Then, the unsaturated fatty acid is cooled to complete a separation process. Thereafter, since a peroxide value (POV) is not more than 10 milimol per kilogram even though about three weeks elapse, the bad smell is not generated.

As described above, since the MSG by-product is added to the fish oil to remove the phospholipid, and then the pre-heating, the deodorization and the cooling processes at the atmosphere of vacuum lower the degree of degeneration, the deodorization of the smell of the fish oil can be accomplished at an extremely low cost and through a simple process. Also, the low POV can be maintained for a long time, the fish oil can be kept for a long time.

Disclosed in Korean Pat. No. 123840 (corresponding to U.S. Pat. No. 5,693,358, yielded on Dec. 2, 1997) is a method for powdering the fish oil obtained from the above method. The method comprises heating a mixture of fish oil with water and an MSG by-product with stirring, reacting the mixture at an elevated temperature in the presence of urea as a catalyst with stirring and fermenting the mixture with steams, separately eradicating water and phospholipids from the fermented fish oil, and powdering the fish oil by adding quicklime, cooling, saponification, salting-out and rolling. After being mixed with animal feed, the powdered quicklime-added fish oil is provided for poultry.

When the resulting animal feed is provided to egg-laying hens, there can be obtained eggs whose yolks contain EPA and DHA. Chickens or pigs which are bred with the feed provide chicken meat or pork transposed by omega 3 fatty acids, such as EPA and DHA. Feeding of the feed to milk cows results in the production of the milk containing omega 3 fatty acid such as DHA at relatively low costs.

Since DHA is known to play an important role in improving retina reflex and intelligence development, the provision of such omega 3 fatty acids is helpful in ensuring children to have sound bodies and improved intelligence.

SUMMARY OF THE INVENTION

Based on the deodorization process of fish oil described in the above-mentioned patents, the present invention pertains to the manufacture of refined fish oil for use as a healthy subsidiary food.

Therefore, it is an object of the present invention to provide a method for manufacturing refined fish oil completely deprived of fish odor.

It is another object of the present invention to provide a method for manufacturing refined fish oil which is highly stable and preservable for a long period of time.

It is a further object of the present invention to provide a method for manufacturing refined fish oil with which omega 3 fatty acids, including EPA and DHA, can be readily provided for humans.

In the present invention, the starting material is the refined fish oil obtained according to the preceding patents of the present inventor. That is, mixture of fish oil, water and an MSG by-product is heated to 20–40° C. while stirring, fermenting the mixture at an elevated temperature of 40–60° C. in the presence of urea as a catalyst, adding steam to the mixture, followed by removing phospholipid components and aqueous components from the fish oil in a centrifuge to give the starting material. Introduction of the process of the present invention into this refined fish oil gives more refined fish oil which is completely deprived of fish odor and can be preserved for a long period of time.

In one embodiment of the present invention, there is provided a method for manufacturing refined fish oil, comprising the steps of: preparing phospholipid-deprived fish oil by mixing fish oil with water and a monosodium glutamate (MSG) by-product while stirring and heating to 20–40° C., fermenting the mixture at an elevated temperature of 40–60° C. in the presence of urea, adding steam to the mixture, and centrifuging the mixture to separate water and phospholipids from the fresh oil, said urea serving as a catalyst; measuring acid value of the separated fish oil and neutralizing the fish oil with NaOH, washing the deaciding fish oil with warm water, and drying the washed fish oil in a vacuum; mixing the dehydrated fish oil with powders of earthworm excrement with a particle size of 150–200 mesh to absorb the fish oil into the powders, stirring the mixture at a temperature of at least 30° C. or higher for 0.5–1 hour, bleaching the fish oil absorbed into the earth worm excrement powders by use of activated clay, and filtering the bleached fish oil through a filter; and deodorizing the bleached and filtered fish oil at a predetermined temperature for a period of time under a steam atmosphere in a high vacuum, deodorizing apparatus, cooling and filtering the deodorized fish oil, and packaging the fish oil in a closed vessel.

In one aspect of the embodiment, the starting fish oil mixture comprises 100 parts by weight of fish oil, 50–70 parts by weight of water, and 10–30 parts by weight of the MSG by-product.

In another aspect of the embodiment, the urea is added at an amount of 0.5–2.0% by weight based on the weight of the starting fish oil mixture.

In a further aspect of the embodiment, the earthworm excrement powders are added at an amount of 0.2–0.5% by weight based on the weight of the starting fish oil mixture.

In still another aspect of the embodiment, the earthworm excrement powders are prepared by collecting earthworm excrements from the soil surface of an earthworm-breeding farm, drying the collected earthworm excrements to a moisture extent of 7–8%, and pulverizing the dried earthworm excrements into powders.

DETAILED DESCRIPTION

Figure 1:
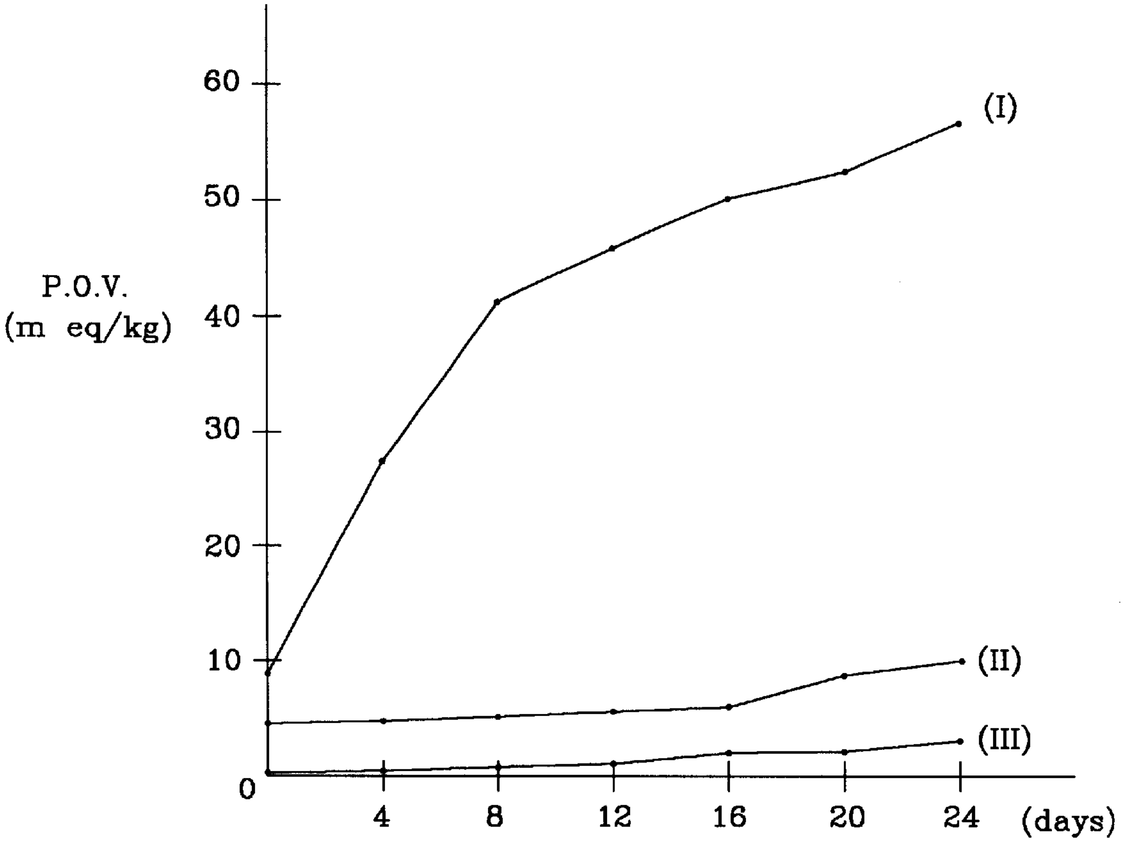
FIG. 1 is a graph showing the peroxide value (POV) changes of the fish oils processed according to conventional methods and the present invention with regard to the time period of the storage life of fish oils.

The present invention may be understood more readily by reference to the following detailed description of preferred embodiment of the invention and the figures.

Before the present method for manufacturing refined fish oil is disclosed or described, it is to be understood that the terminology used herein is for the purpose of describing particular embodiments only and is not intended to be limiting. It must be noted that, as used in the specification and the appended claims, the singular forms "a", "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

First Process

This process is conducted in a similar manner to the first and the second step described in U.S. Pat. No. 5,693,358 which discloses an animal feed manufacturing method based on fish oil.

50–70 parts by weight of water and 10–30 parts by weight of an MSG by-product are mixed with the fish oil, and the mixture is gradually heated to 20–40° C. with stirring. To the mixture, urea is added at an amount of 0.5–2.0% by weight based on the weight of the starting fish oil mixture, followed by fermentation at 40–60° C. 3–6 hours after the fermentation, the mixture is further processed with steam at 90–95° C. and water and phospholipids are separated from the fish oil in a centrifuge. The added urea serves as a catalyst which accelerates the transposition process in which the oil-soluble phospholipids of fish oil is converted into water-soluble ones as a result of reacting with the water-soluble proteins by the MSG by-product.

Second Process

The fish oil separated is measured for acid value, neutralized with NaOH, and deprived of soap components. Free alkali contained in the deaciding fish oil is removed by washing with warm water. Thereafter, the fish oil is dried under vacuum.

Third Process

To the completely dried fish oil of the Second Process, powder (particle size 150–200 mesh) of earthworm excrement is added at an amount of 0.2–0.5% by weight based on the weight of the starting fish oil mixture. Stirring at 30–40° C. of the mixture makes the fish oil absorbed into the excrement powder. After 0.5–1 hour, the fish oil-absorbed earthworm excrement powder is mixed with activated clay to absorb the pigment and color material followed by filtering through a filter.

The preparation of the powder of earthworm excrements is conducted as follows: first, the excrements of earthworms are dried. The excrements can be obtained by collecting from the soil surface of earthworm-breeding farms. The drying is conducted to the extent that the moisture content of the collected excrements is reduced from about 30% to 7–8%. Subsequently, the dried earthworm excrements are pulverized into powders.

Fourth Process

In a well-known high vacuum, deodorizing apparatus, the bleached and filtered fish oil is subjected to deodorization at 160–180° C. for 4–8 hours under a steam pressure of 3 kg/cm$^2$. During this procedure, the unsaturated low fatty acids are removed by distillation from the fish oil. After being rapidly cooled in the same vacuum level to remove water, the fish oil is stored in a closed vessel which is then filled with nitrogen gas to improve the life span of the fish oil.

The refined oil prepared above may be packaged in individual units which are suitable for use immediately. The filling of nitrogen gas in the individual packages renders the refined oil to be kept fresh for a relatively long period of time. Of course, storing in a refrigerator is also helpful in keeping the fish oil fresh for an extended period of time.

For various fishes, a measurement was made of qualities of the fish oil obtained according to the First to the Fourth Process above and the results are given in Tables 1 to 4, below. For instance, sardine oil was greatly improved from 3.79 to 0.47 mg KOH/g in acid value, from 9.29 to 1.24 meq/kg in peroxide value (POV), and from 10$^+$ to 3$^+$ Gardner in color, as shown in Table 1.

TABLE 1

Sardine Fish Oil

| Properties | Crude Fish Oil | Refined Fish Oil |
|---|---|---|
| Acid Value (mg KOH/g) | 3.79 | 0.47 |
| P.O.V. (m eq/kg) | 9.29 | 1.24 |
| color (Gardner) | 10$^+$ | 3$^+$ |
| D.H.A($C_{22:6}$) | 11.83 | 11.63 |
| E.P.A($C_{20:5}$) | 19.05 | 18.62 |

TABLE 2

Squid Liver Oil

| Properties | Crude Fish Oil | Refined Fish Oil |
|---|---|---|
| Acid Value (mg KOH/g) | 23.07 | 0.12 |
| P.O.V. (m eq/kg) | 12.25 | 0.09 |
| color (Gardner) | $11^{+}$ | $4^{+}$ |
| D.H.A($C_{22:6}$) | 24.15 | 23.65 |
| E.P.A($C_{20:5}$) | 10.64 | 10.92 |

TABLE 3

Tuna Orbic Tissue Oil (From Thailand)

| Properties | Crude Fish Oil | Refined Fish Oil |
|---|---|---|
| Acid Value (mg KOH/g) | 3.56 | 0.17 |
| P.O.V. (m eq/kg) | 7.08 | 0.73 |
| color (Gardner) | $9^{+}$ | $4^{+}$ |
| D.H.A($C_{22:6}$) | 27.72 | 27.14 |
| E.P.A($C_{20:5}$) | 6.42 | 6.89 |

TABLE 4

Tuna Orbic Tissue Oil (from Dong Won Industries, Korea)

| Properties | Crude Fish Oil | Refined Fish Oil |
|---|---|---|
| Acid Value (mg KOH/g) | 2.06 | 0.29 |
| P.O.V. (m eq/kg) | 3.57 | 0.65 |
| color (Gardner) | $7^{+}$ | $3^{+}$ |
| D.H.A($C_{22:6}$) | 29.28 | 28.90 |
| E.P.A($C_{20:5}$) | 9.93 | 9.84 |

With reference to FIG. 1, there is a graph in which POV are plotted with regard to a time period of the storage life of sardine oils refined according to various techniques.

In the graph, the POV changes of a conventional refined sardine oil, the refined sardine oil obtained after the first and the second step of U.S. Pat. No. 5,693,358, and the refined sardine oil of the present invention are represented by curves I, II and III, respectively.

When tracing Curve II, the POV of the sardine oil obtained according to the U.S. Pat. No. 5,693,358 was 4.2 meq/kg just after refinement and was increased to 8.5 meq/kg after a lapse of 20 days at 60° C. In contrast, the sardine oil obtained according to the present invention showed a POV of 1.24 meq/kg just after refinement and the POV was increased only to as low as about 2.5 meq/kg after a lapse of 20 days at the same condition. Therefore, the fish oil refined according to the present invention can be preserved freshly for a relatively longer period of time than conventional ones.

As described hereinbefore, the present invention provides refined fish oil which is almost completely deodorized by removing phospholipids from fish oil, absorbing the fish oil into powdered earthworm excrements, bleaching the mixture with activated clay and filtering the mixture.

The fish oil refined according to the method of the present invention is significantly lowered in acid value and POV compared with crude oil. 20 days after the refinement, the POV of fish oil remains as low as 2.5 or less, so that a great improvement can be brought about in the stability and preservation ability.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for manufacturing refined fish oil, which method comprises the steps of:

preparing phospholipid-deprived fish oil by mixing fish oil with water and a monosodium glutamate (MSG) by-product while stirring and heating to 20–40° C. to form a starting fish oil mixture, fermenting the mixture at an elevated temperature of 40–60° C. in the presence of urea, adding steam to the mixture, and centrifuging the mixture to separate water and phospholipids from the fish oil, said urea serving as a catalyst;

measuring the acid value of the separated fish oil, neutralizing the fish oil with NaOH, washing the fish oil with warm water, and drying the washed fish oil in a vacuum;

mixing the dehydrated fish oil with powders of earthworm excrement with a particle size of 150–200 mesh to absorb the fish oil into the powders, subjecting the mixture to stirring at a temperature of at least 30° C. or higher for 0.5–1 hour, bleaching the fish oil absorbed into the earthworm excrement powders by mixing with activated clay, and filtering the bleached fish oil through a filter; and deodorizing the bleached and filtered fish oil and at a predetermined temperature under a steam atmosphere in a high vacuum deodorizing apparatus, cooling and filtering the deodorized fish oil, and packaging the fish oil in a closed vessel.

2. The method as set forth in claim 1, wherein the mixture comprises 100 parts by weight of fish oil, 50–70 parts by weight of water and 10–30 parts by weight of the MSG by-product.

3. The method as set forth in claim 1, wherein the urea is added at an amount of 0.5–2.0% by weight based on weight of the starting fish oil mixture.

4. The method as set forth in claim 1, wherein the earthworm excrement powders are added at an amount of 0.2–0.5% by weight based on the weight of the starting fish oil mixture.

5. A method as set forth in claim 1, wherein the earthworm excrement powders are prepared by collecting earthworm excrements from the soil surface of an earthworm-breeding farm, drying the collected earthworm excrements to a moisture extent of 7–8%, and pulverizing the dried earthworm excrements into powders.

6. A method as set forth in claim 1, wherein the deodorizing step is conducted by heating the bleached and filtered fish oil at 160–180° C. for 4–8 hours in a steam pressure of 3 kg/cm$^2$ or less.

7. A method as set forth in claim 1, wherein the closed vessels are filled with nitrogen gas.

8. The method as set forth in claim 1, wherein the fermentation is conducted for 3–6 hours in the presence of urea and steam is added at 90–95° C.

9. The method as set forth in claim 1, wherein the fermentation is conducted for 3–6 hours.

* * * * *